US012689314B2

(12) United States Patent
Regnier et al.

(10) Patent No.: US 12,689,314 B2
(45) Date of Patent: Jul. 21, 2026

(54) PENDULAR UNIT WITH A MONOLITHIC INERTIAL MASS MOUNTED ON A PIEZOELECTRIC BEAM, IN PARTICULAR FOR AN ENERGY HARVESTER IN A LEADLESS AUTONOMOUS CARDIAC CAPSULE

(71) Applicant: CAIRDAC, Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 690 days.

(21) Appl. No.: 18/315,222

(22) Filed: May 10, 2023

(65) Prior Publication Data

US 2024/0120856 A1 Apr. 11, 2024

(30) Foreign Application Priority Data

Oct. 11, 2022 (EP) ..................................... 22315236

(51) Int. Cl.
*H02N 2/18* (2006.01)
*H02N 2/00* (2006.01)
*A61N 1/378* (2006.01)

(52) U.S. Cl.
CPC ............. *H02N 2/186* (2013.01); *H02N 2/181* (2013.01); *H02N 2/22* (2013.01); *A61N 1/3785* (2013.01)

(58) Field of Classification Search
CPC .......... H02N 2/186; H02N 2/181; H02N 2/22; H10N 30/03; H10N 30/306; A61N 1/3785; A61N 1/3756
See application file for complete search history.

(56) References Cited

U.S. PATENT DOCUMENTS

| | | | |
|---|---|---|---|
| 3,456,134 A | 7/1969 | Ko | |
| 2018/0185638 A1* | 7/2018 | Regnier | ............... A61N 1/3756 |
| 2019/0381325 A1 | 12/2019 | Regnier et al. | |

FOREIGN PATENT DOCUMENTS

| | | |
|---|---|---|
| JP | 2011-066970 A | 3/2011 |
| WO | 2005/067073 A1 | 7/2005 |

OTHER PUBLICATIONS

European Patent Office, Search Report issued in corresponding Application No. EP 22 31 5236, mailed Feb. 13, 2023 (English-language translation not available).

* cited by examiner

*Primary Examiner* — Emily P Pham
(74) *Attorney, Agent, or Firm* — Stites & Harbison, PLLC; Jeffrey A. Haeberlin

(57) ABSTRACT
The pendular unit comprises a piezoelectric transducer beam (22), and an inertial mass mounted at the free distal end of the beam (22). The inertial mass (26) is a monolithic part including a cavity in the form of an axial slit (64), with two opposite longitudinal surfaces (74) extending along a central axis of the inertial mass (26). The axial slit (64) opens out on the proximal side of the inertial mass (26), and receives the free distal end of the beam (22), secured between the two opposite longitudinal surfaces (74) of the axial slit (64).

15 Claims, 8 Drawing Sheets

PENDULAR UNIT WITH A MONOLITHIC INERTIAL MASS MOUNTED ON A PIEZOELECTRIC BEAM, IN PARTICULAR FOR AN ENERGY HARVESTER IN A LEADLESS AUTONOMOUS CARDIAC CAPSULE

TECHNICAL FIELD

Background of the Invention

The invention relates to energy harvesting devices, also called "harvesters" or "scavengers", which collect the mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limiting the invention, whose teachings can be applied to many other types of autonomous devices incorporating an energy harvester of the PEH type, whether these devices are implantable or not, medical or not.

STATE OF THE ART

In the field of medical implants, the recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage component. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of autonomous devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a body of very small size able to be implanted at sites of difficult access or leaving little available space, such as the ventricle apex, the inner wall of the atrium, etc.

WO 2019/001829 A1 (Cairdac) describes an example of such a leadless intracardial capsule.

The invention more particularly relates to capsules or similar implantable devices whose energy harvester is of the PEH type, i.e. using a Piezoelectric Transducer or "PZT" and an inertial pendular unit subjected to the external stresses described hereinabove. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, oscillates at a natural free oscillation frequency.

The mechanical energy of the oscillation is converted into electrical energy by a mechanical-electrical transducer producing an electrical signal. This mechanical-electrical transducer may be in particular a PZT that is cyclically stressed in bending so as to generate within its constituent material electrical charges that are collected at the surface of the component to be used by the self-powering system of the leadless capsule. The PZT is most often in the form of a beam clamped at one of its end and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage component.

The mechanical structure of such an energy harvester of the PEH type is described in detail in particular in WO 2018/122244 A1 (Sorin CRM/Regnier).

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

In the PEH structures proposed up to now, for example by above-mentioned WO 2018/122244 A1, the inertial mass is made up of two identical half-masses, arranged symmetrically on either side of the PZT beam. These two half-masses form together a truncated cone and are fastened to the free end of the beam, on either side of the latter, by bonding.

The conicity of the inertial mass outer surface makes it possible to optimize the available space before entering into contact with the inside of the tube that contains the PEH. This geometry is however not exhaustive and may be adapted to its environment to optimize the mass/bulk ratio.

The material used for the inertial mass is a metal, generally a molded tungsten, that has a high density for a controlled cost price, and the size of the seismic mass is adjusted as a function of the final weight required for the desired vibratory mode, taking into account the PZT beam geometry and elasticity.

The problem of the invention finds its source in the difficulties encountered due to the way the inertial mass is assembled to the PZT beam, by bonding of the metal of each half-masses to the faces of the ceramic PZT beam.

First, the presence of a chemical binding material at the metal/ceramic interface has an impact on the lifetime of the PEH. Even with a perfect control of the glues and implementation thereof, it has not been possible up to now to guarantee more than 10 years lifetime without risk of failure. This ten-year figure (corresponding to about 300 million cardiac cycles) is that usually retained for the conventional cardiac pacemakers, the generator of which has anyway to be replaced at this deadline taking into account the depletion of the built-in power battery; on the other hand, in the case of a leadless pacemaker, which is difficult to explant to be replaced by a new device, the guarantee of a far longer lifetime would be needed, typically 20 years of continuous operation without failure.

However, the glues used up to now do not allow guaranteeing such a performance, even for those which degrade only slightly over time.

A second problem lies in the difficulty to correctly control the bonding process at the time of manufacturing the PEH. This process is in itself very delicate to implement due to the very reduced sizes of the parts, the necessity to operate under controlled atmosphere and to avoid any chemical pollution by contaminants liable to modify the ageing resistance properties of the bonding performed.

A third problem lies, during this bonding process, in the particular difficulty of perfectly controlling the amount of glue used: an insufficient quantity of glue obviously reduces the solidity of the final bonding obtained, but, conversely, an excess of glue results in glue effusion beyond the metal/ceramic interface, with a risk of altering the flexibility of the PZT beam (which looses its flexibility at the place where the glue has spilled) with an increase of the natural vibration frequency of the pendular unit, and consequently a disruption of the system inducing a lower energy harvesting by the PEH, all things being equal otherwise.

The object of the invention is to propose a new PEH module structure, and a new method for assembling such a structure, which overcomes the just-exposed difficulties and limitations, by making it possible in particular:

to guarantee the PEH a life duration liable to reach 20 years;

to offer a simplified, economical and non-operator-dependent assembly technique; and to obtain a PEH with perfectly controlled vibratory characteristics, and that way an optimized efficiency of the energy harvesting function.

SUMMARY OF THE INVENTION

To solve these problems and achieve the above-mentioned objects, the invention proposes a pendular unit for a PEH module, this pendular unit comprising, in a manner known per se, in particular from the above-mentioned WO 2018/122244 A1, a piezoelectric transducer, PZT, beam, that is elastically deformable in bending and that extends in axial direction between a clamped proximal end and a free distal end, and an inertial mass, that is mounted at the free distal end of the PZT beam and mobile in transverse direction. The pendular unit is adapted to convert a mechanical energy produced by oscillations of the pendular unit under the effect of external stresses undergone by the module into an oscillating electrical signal collected by surface electrodes of the PZT beam.

Characteristically of the invention, the inertial mass is a monolithic part including a cavity in the form of an axial slit, with two opposite longitudinal surfaces extending along a central axis of the inertial mass, the axial slit opening out on the proximal side of the inertial mass and receiving the free distal end of the PZT beam.

According to various advantageous embodiments:

along the length of the clamping area, the two opposite surfaces comprise flat and parallel symmetrical surfaces separated by a constant radial spacing;

the two opposite surfaces comprise surfaces that widen along the length of the non-clamping area;

the two opposite surfaces are symmetrical surfaces radially separated by an increasing radial spacing, in the proximal to distal direction, along at least part of the length of the axial slit in the longitudinal direction, in such a way as to produce a progressive clamping of the PZT beam, with a maximum clamping force in the clamping area and zero clamping force in the non-clamping area;

in radial direction, the axial slit also opens out in at least one of the inertial mass sides;

at least one of the two opposite surfaces comprise at least one non-return notch provided with an axial and/or radial stop adapted to block the PZT beam in position in the axial slit;

in this latter case, the PZT beam comprises, in an area located between the opposite surfaces of the axial slit, at least one cut adapted to cooperate with an axial and/or radial stop for mating a non-return notch of the inertial mass;

in the clamping area, the minimum value of the radial spacing between the opposite surfaces is equal to a thickness of the PZT beam, to within a negative clearance, in such a way as to exert on the PZT beam a pinching force between the opposite surfaces;

the PZT beam pinching force exerted by the opposite surfaces is between 0.5 and 2 N/mm².

The invention has also for object a method for assembling such a pendular unit, comprising the following steps:

a) obtaining an inertial mass by forming an axial slit in the mass of a monolithic part, the axial slit extending along a central axis of the inertial mass from a proximal end, thus forming two opposite longitudinal surfaces, the axial slit comprising successive cavities with different geometries, comprising: on proximal side, a clamping area in which the PZT beam is secured between the two opposite surfaces of the axial slit; and on distal side, a non-clamping area;

b) inserting into the axial slit the free distal end of the PZT beam; and c) securing the distal end of the PZT beam to the monolithic part between the two opposite surfaces of the axial slit.

According to various advantageous embodiments of this method:

at step a), the formation of the axial slit in the monolithic part is performed using a material removal technique selected among wire electro-erosion or disk machining; or using an additive material deposition technique selected among stereolithography, SLA, selective laser sintering, SLS, or fused deposition modeling, FDM;

at step c), the securing of the distal end of the PZT beam to the monolithic part is performed using a technique selected among: temperature deformation of the PZT beam or of the monolithic part before insertion in step b) and return to room temperature after insertion in step b); elastic deformation of the monolithic part to enlarge the axial slit before insertion in step b) and release after the insertion in step b); bonding; crimping; and/or welding of an added link part.

The invention has also for object a PEH comprising an elongated envelope tube and, contained inside the tube, a pendular unit as hereinabove.

The invention also relates to an autonomous device incorporating in a device body a PEH module as hereinabove, and comprising:

an electronic unit;

a PEH module as hereinabove, outputting an electric signal;

a power management circuit, adapted to rectify and regulate the electric signal produced by the PEH module, to output a stabilized direct power voltage or current; and an energy storage component for powering the electronic unit, said stabilized direct voltage or current provided by the power management circuit being used to power the electronic unit and/or to charge the energy storage component of the autonomous device.

In particular, this autonomous device can be an active medical device of the leadless capsule type, comprising a capsule body with an element for its anchoring to a wall of a patient's organ, and wherein the external stresses to which is subjected the pendular unit of the PEH module are stresses applied to the capsule body under the effect of movements of said wall and/or flow rate variations of a flow in the surrounding environment.

BRIEF DESCRIPTION OF THE DRAWINGS

An exemplary embodiment of the present invention will now be described with reference to the appended drawings, in which the same references denote identical or functionally similar elements throughout the figures.

DETAILED DESCRIPTION OF PREFERENTIAL EMBODIMENTS OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of autonomous devices incorporating an energy harvester of the PEH type, whether these devices are implantable or not, medical or not.

Figure 1:
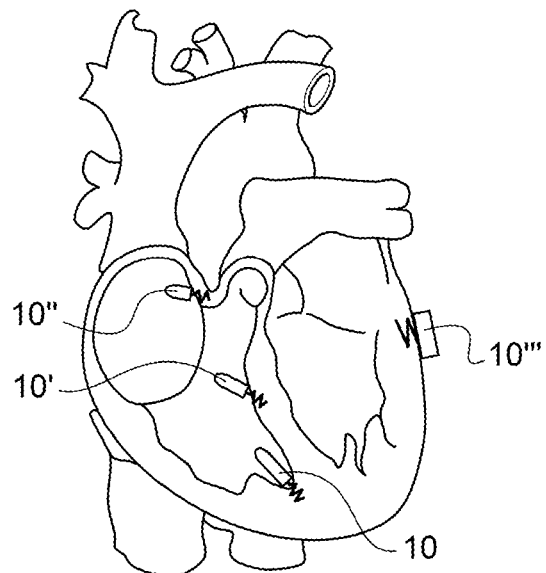
FIG. 1 illustrates medical devices of the leadless capsule type in their environment, with various examples of implantation sites in, on or near a patient's heart.

FIG. 1 shows various possibilities of implantation sites for a leadless type device in an application to cardiac pacing. Therefore, the capsule 10 is implanted inside a cavity of the myocardium (endocavitary implant), for example at the apex of the right ventricle. As an alternative, the capsule may also be implanted on the right interventricular septum, as in 10', or also on an atrial wall, as illustrated in 10". The device may also be an epicardial capsule placed on an external region of the myocardium, as illustrated in 10'".

In any case, the leadless capsule is attached to the heart wall by means of a protruding anchoring system intended to enter the heart tissue for the holding on the implantation site. Other anchoring systems can be used, and do not change in any way the implementation of the present invention. Capsule 10 has the external form of an implant with an elongated tubular body 12 enclosing the various electronic and power supply circuits of the capsule, as well as an energy harvester with a pendular unit. The typical size of the known capsules is about 6 mm diameter for about 25 to 40 mm length.

Tubular body 12 has, at its front (distal) end 14, a protruding anchoring element, for example a helical screw 16, to hold the capsule on the implantation site. Other anchoring systems can be used, and do not change in any way the implementation of the present invention. The opposite (proximal) end 18 of capsule 10 is a free end, which is only provided with means (not shown) for the temporary connection to a guide-catheter or another implantation accessory used for implantation or explanation of the capsule, which is then detached from the latter.

Figure 2:
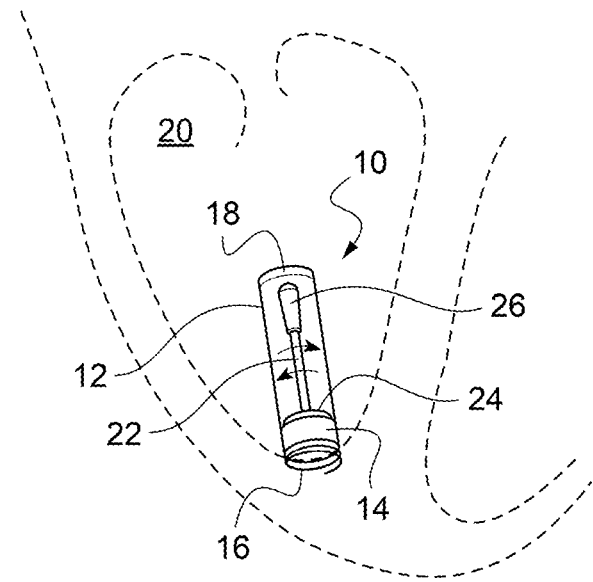
FIG. 2 illustrates a leadless capsule implanted in the bottom of the right ventricle of a patient.

In the example illustrated in FIG. 2, leadless capsule 10 is an endocavitary implant implanted into a cavity 20 of the myocardium, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

Figure 3:
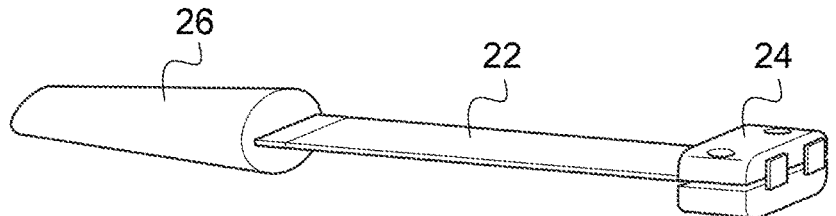
FIG. 3 shows as such a pendular unit of a known type, with a PZT in the form of an elongated beam clamped at one end and supporting an inertial mass at its opposite end.

The pendular unit, illustrated as such in FIG. 3, is made up of a piezoelectric beam 22 secured to a clamping part 24 at one of its ends (hereinafter the "proximal end" of the beam), and whose opposite, free end (hereinafter the "distal end" of the beam) is coupled to a mobile inertial mass 26. Piezoelectric beam 22 is an elastically deformable flexible beam that constitutes, with the inertial mass 26, a pendular system of the mass-spring type. Due to its inertia, mass 26 subjects beam 22 to a deformation of the vibratory type on either side of a neutral or non-deformed position corresponding to a stable rest position in the absence of any stress. The typical minimum size of PZT beams of the known devices of this type is of the order of 25 mm long for about 5 mm width.

Actually, as for its mechanical behavior, this unit may be equated to a "clamped/free beam" structure, having a natural oscillation frequency, which is herein the frequency at which the mass-spring system oscillates. It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 22 further performs, by piezoelectric effect, a mechanical-electrical transducer function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 4:
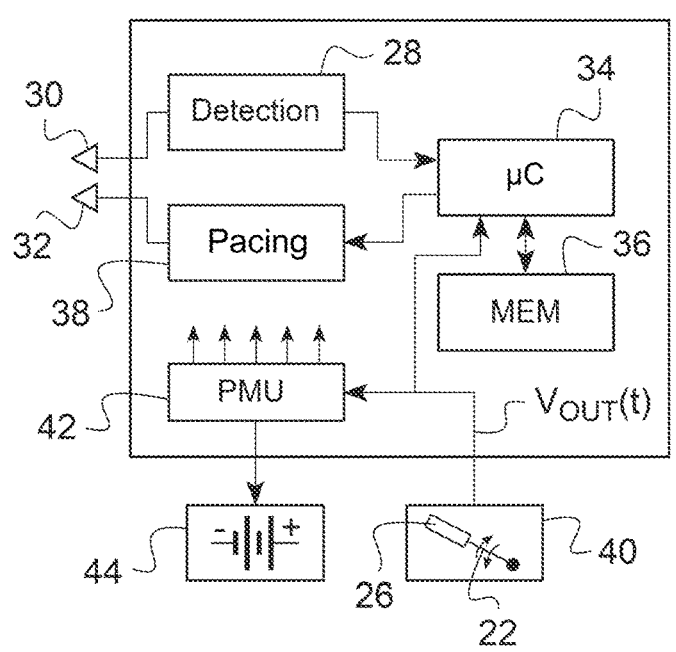
FIG. 4 schematically shows the main functional blocks of a leadless capsule.

FIG. 4 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to provide to the system of electrodes 30, 32 myocardial pacing pulses.

An energy harvesting circuit or PEH 40 is moreover provided, made up of the pendular unit formed by piezoelectric beam 22 and inertial mass 26, described hereinabove with reference to FIGS. 2 and 3. As piezoelectric beam 22 also ensures a mechanical-electrical transducer function, it converts into electrical charges the mechanical stresses undergone and produces a variable electrical signal $V_{OUT}(t)$, which is an alternating signal oscillating at the natural oscillation frequency of the pendular beam 22/mass 26 unit, and at the rhythm of the successive beats of the myocardium to which the capsule is coupled.

The variable electrical signal $V_{OUT}(t)$ is sent to a power management circuit or PMU 42. PMU 42 rectifies and regulates the signal $V_{OUT}(t)$ so as to output a stabilized direct voltage or current for powering the various electronic circuits and charging the integrated battery 44.

On the other hand, the beam is advantageously a beam of the bimorphous type, i.e. capable of generating energy on its two faces when subjected to a deformation. Theses transduction properties are typical of a piezoelectric material, such as PZT ceramics or PMN-PT, barium titanate or lithium niobate mono-crystals.

Figure 5:
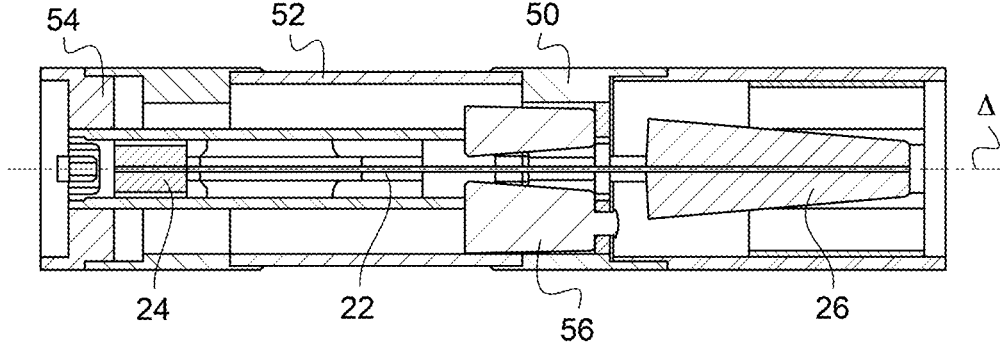
FIG. 5 is a cross-sectional view, along an axial plane, of the PEH module according to the invention.
Figure 6:
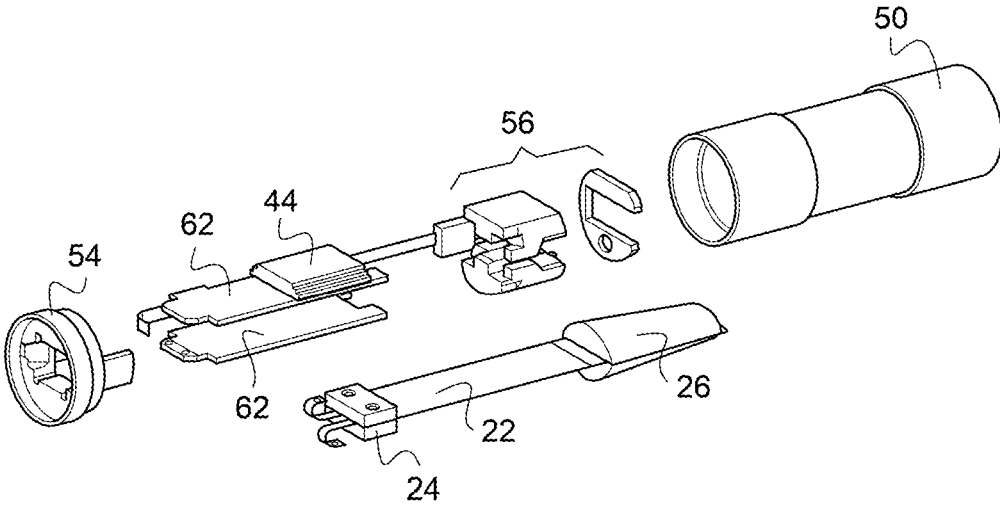
FIG. 6 is an exploded perspective view showing the different elements of the PEH module of FIG. 5.

In FIGS. 5 and 6 are shown the main elements of a PEH module according to the invention.

These different elements are contained inside an envelope tube 50, that is generally a metal tube (to allow welding operations that will be described hereinafter), preferably made of titanium due to the excellent biocompatibility of this metal.

An envelope tube particularly suitable for making a leadless capsule is described in particular in EP 3 730 185 A1 (Cairdac), corresponding to US 2020/338241 A1 (Regnier et al.), that illustrates in particular a metal/ceramic composite tube having a central portion (52 in FIG. 5) made of a radio-frequency transparent ceramic material, in such a way as to allow a wireless communication between electronic circuits located inside the tube and the outer environment, the rest of the tube being made of a metal material such as titanium, the whole forming a one-piece tubular unit.

Envelop tube 50 contains the pendular unit made up of the beam 22 held on the proximal side by clamping part 24 and carrying the inertial mass 26 on the distal side. The pendular unit is placed at the center of envelope tube 50 and aligned on axis Δ of the tube.

In the following, it will be understood by "axial direction", the direction of greater length of the beam, and by "transverse direction", the direction of deformation of the beam, a direction that is located in a radial plane and that is perpendicular to the axial direction Δ; the direction perpendicular to the axial and transverse directions will be called "lateral direction".

Clamping part 24 is held in the tube by a mount 54 secured to the tube, in particular a mount made of a metal material such as titanium, capable of being peripherally welded to the tube in such a way as to secure mount 54, and hence clamp 24 and beam 22, to tube 50.

EP 3 892 325 A1 (Cairdac), corresponding to US 2021/316148 A1 (Regnier et al.), describes in detail an example of clamping part and mount, and reference can be made to this document for more details.

Tube 50 also contains one or several printed circuit boards (PCBs) 62, in the example illustrated two PCBs 62, one of which carries battery 44. These two PCBs are connected to each other by a sheet of flexible conductors and supported at each of their ends, on distal side by insert 56 and on proximal side by mount 54, respectively.

The configuration of these PCBs on either side of the beam 22, and the way they are connected by a flexible sheet and supported between a proximal element and a distal element are described in particular in above-mentioned US 2019/381325 A1, to which reference can be made for more details.

Insert 56 is for example a summarization insert as that described in pending application U.S. Ser. No. 18/151,579 in the name of the applicant, entitled "Piezoelectric energy harvester with a controlled-deflection beam, in particular for powering a leadless autonomous cardiac capsule".

This summarization insert makes it possible to preserve the maximum oscillation amplitude of the beam by avoiding it to be reduced by a sub-optimal positioning of the pendular unit in the body of the module, in particular due to an imperfect positioning (off-centering, misalignment) of the inertial mass 26.

The invention more particularly relates to the way the just-described inertial mass 26 of the leadless capsule pendular unit is made and assembled.

FIGS. 7 to 14 illustrate various embodiments according to the invention, and FIGS. 15 to 18 illustrate the method of making a leadless capsule provided with such a pendular unit.

Figure 7:
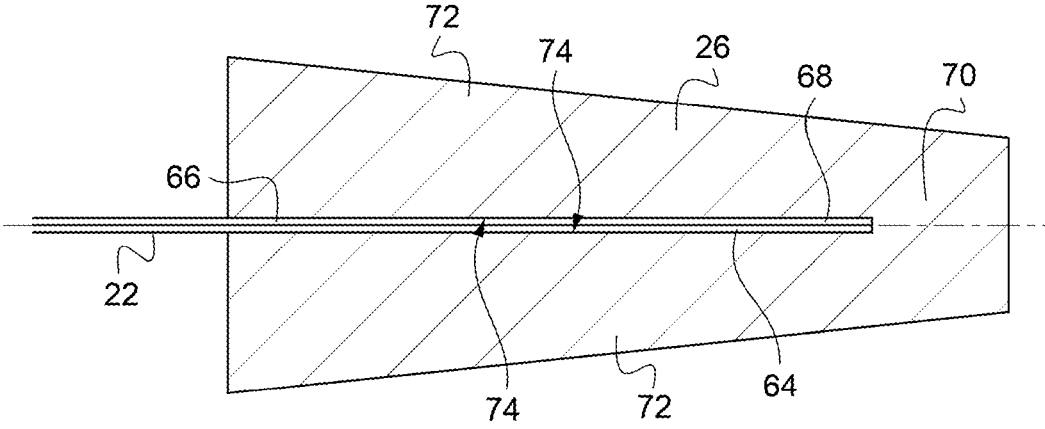
FIG. 7 is a cross-sectional view, along an axial plane, of an inertial mass of a pendular unit according to a first embodiment of the invention.

FIG. 7 is a cross-sectional view, along an axial plane, of a pendular unit according to a first embodiment of the invention.

The inertial mass 26 is formed of a single one-piece part, machined in a bulk mass, approximately frustoconical in shape. In this part has been formed a cavity 64 in the form of an axial slit, typically using a known material removal machining technique with a disk that transversally removes the material at the center of the part, or also using a wire electro-erosion technique.

As an alternative, it is possible to form cavity 64 using additive material deposition techniques such as stereolithography (SLA), selective laser sintering (SLS) or fused deposition modeling (FDM), for example.

The material constituting the inertial mass 26 is advantageously tungsten (or also platinum, osmium, gold, iridium or any other high volume density material), which allows obtaining a relatively high mass for a reduced volume.

The slit forming axial cavity 64 extends from a proximal through-end 66 to a distal blind-end 68, in such a way as to leave at this end 68 an intact, unmachined portion 70, in the bottom of the cavity. Once machined, the part has then a core area that corresponds to the intact portion 70 from which extend two legs 72, the whole forming a single-piece part. The slit forming axial cavity 64 defines two opposite inner faces 74, 74, facing each other, forming bearing surfaces for sandwiching the distal end of the PZT beam 22. In this embodiment, the two surfaces 74, 74 of cavity 64 are parallel along the whole slit length, from proximal end 66 to distal end 68. To allow a pinching of the beam, the height of the slit between the facing surfaces 74 is slightly lower, to within an operational clearance, to the thickness of the PZT beam 22 that will be introduced after the machining of the slit forming axial cavity 64, in such a way as to constrain the assembly by a permanent effort on the portion (or the totality) of the surfaces 74 that is in contact with the corresponding outer surfaces of the PZT beam 22.

A permanent assembly of the unit can thus be obtained without addition of material, in particular without addition of glue and without added parts need to be provided to secure the inertial mass 26 to the PZT beam 22.

This operation of mounting the PZT beam 22 into cavity 64 of the inertial mass 26 may be performed using various techniques, such as:

temperature deformation of the PZT beam 22 and/or of the inertial mass 26 before insertion of the PZT beam 22 into cavity 64, then return of the unit to room temperature after insertion;

elastic deformation of the inertial mass 26 by forced spacing apart of the two legs 72 to enlarge slit 64 (by spacing the facing inner surfaces 74) before insertion of the PZT beam 22, then release after insertion of the latter;

bonding, crimping and/or welding of an added link part for immobilizing between each other the PZT beam 22 and the inertial mass 26 (the two preceding techniques being however preferred).

Figure 8:
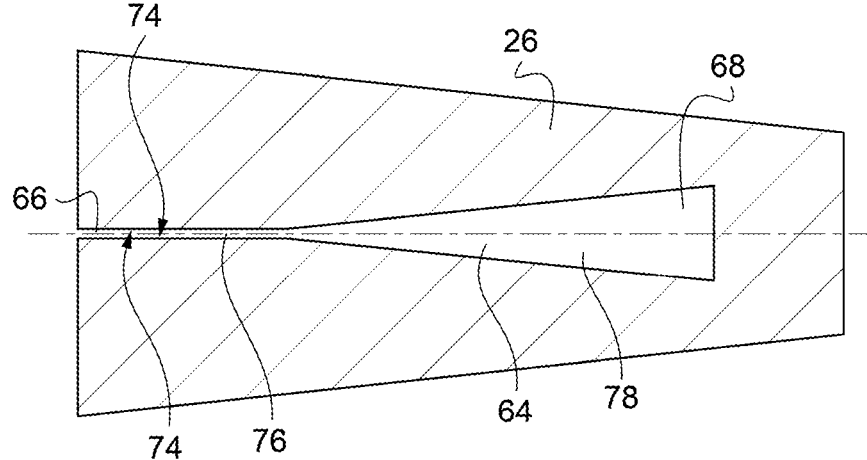
FIG. 8 is a cross-sectional view, along an axial plane, of an inertial mass of a pendular unit according to a second embodiment of the invention.

FIG. 8 is similar to FIG. 7, for a second embodiment of the invention.

In this embodiment, in order to reduce the surface areas in contact with the beam, the slit forms successive cavities with different geometries. In the illustrated example, cavity 64 comprises a first portion 76 with two flat and parallel, facing surfaces 74, 74 (as in the preceding embodiment), but the length in axial direction from proximal end 66 of this first portion is more reduced, and the cavity then widens at a second portion 78, up to distal end 68.

This configuration makes it possible to have two functionally different areas, with a clamping area corresponding to the most proximal portion 76 and a non-clamping area 78 corresponding to the rest of the cavity length. The PZT beam 22 will exert the pinching force only in area 76 between the two parallel bearing surfaces 74, 74. This force being higher (more reduced contact surface area), it will be advisable to control the pressure exerted on the PZT beam in such a way as not to damage the latter, by limiting the effort to a value typically between 0.5 and 2 N/mm². The multi-cavity geometry of this second embodiment may be obtained using known techniques such as wire electro-erosion; as regards the securing of the PZT beam to the inertial mass 26, the various techniques exposed hereinabove for the first embodiment can be used.

Figure 9:
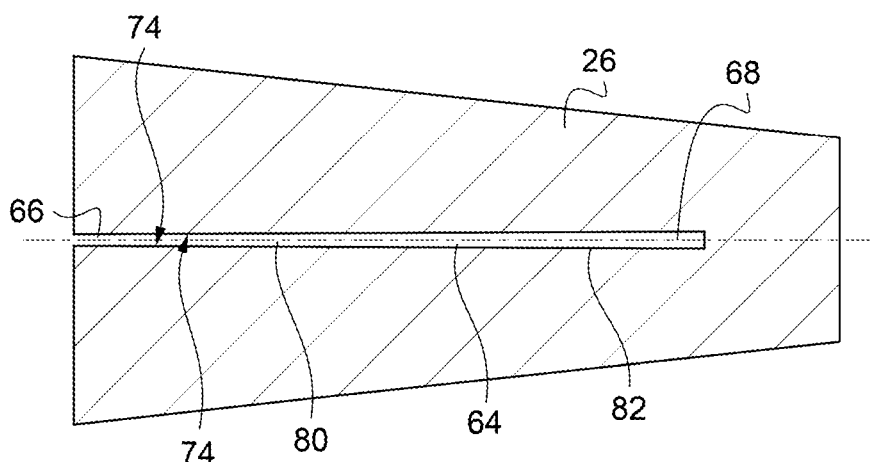
FIG. 9 is a cross-sectional view, along an axial plane, of an inertial mass of a pendular unit according to a third embodiment of the invention.
Figure 10:
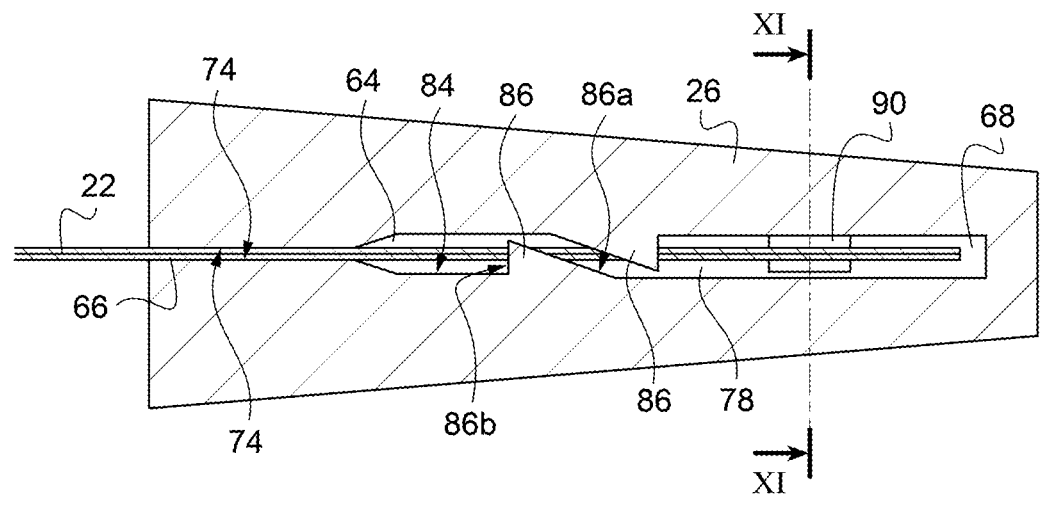
FIG. 10 is a cross-sectional view, along an axial plane, of an inertial mass of a pendular unit according to a fourth embodiment of the invention.
Figure 11:
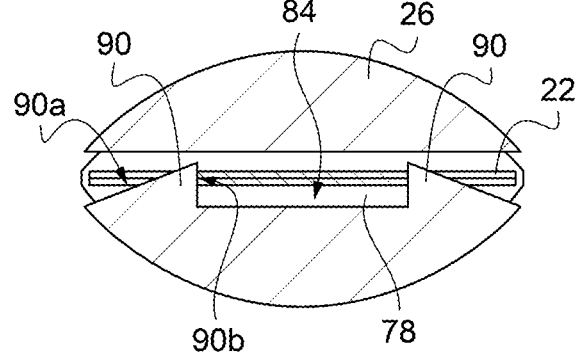
FIG. 11 is a cross-sectional view, along radial plane XI-XI in FIG. 10, of the inertial mass of the pendular unit of FIG. 10.
Figure 12:
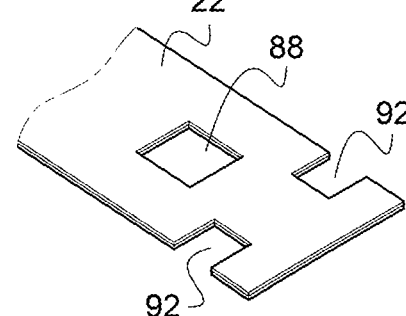
FIG. 12 is a perspective view showing, as such, the configuration of the end of the PZT beam of the pendular unit of FIG. 10.

FIG. 9 is similar to FIGS. 7 and 8, for a third embodiment of the invention. In this embodiment, the facing surfaces 74, 74 are surfaces that are flat but not parallel: the slit width increases progressively from proximal end 66 to distal end 68. At proximal end 66, the spacing in radial direction between the surfaces 74, 74 is lower than the PZT beam thickness, to within a negative clearance, whereas at distal end 68, this spacing is not lower than the beam thickness.

Once the PZT beam introduced into cavity 64 (using one of the techniques exposed hereinabove), the two facing surfaces 74, 74 conform the beam shape and are in a parallel configuration, imparting a progressive clamping of the inertial mass 26 to the beam, the clamping force being maximal in area 80 at proximal end 66 and zero in area 82 at distal end 68.

FIGS. 10 to 14 illustrate a fourth embodiment of the invention.

In this embodiment, axial cavity 64 includes, as in the embodiment illustrated in FIG. 8, two distinct portions, with, on proximal side, a portion including the two facing faces 74, 74 forming bearing surfaces, intended to sandwich and immobilize the PZT beam 22. In the rest of the cavity, an enlarged portion 78 forms up to distal end 68 a non-clamping area, receiving the PZT beam but exerting no clamping pressure to the latter.

In enlarged portion 78, the facing faces 84 of cavity 64 have suitable geometries to immobilize, axially and coaxially, the inertial mass 26 with respect to the PZT beam 22, by notching effect. These geometries are for example formed of notches 86, 90 with, in the illustrated example and in a non-limiting way, two axial immobilization notches 86 directed in opposite directions, and two radial immobilization notches 90, also directed in opposite directions.

Axial immobilization notches 86 each have a ramp-shaped inclined face 86a directed in axial direction, forward for one the notches 86 and rearward for the other notch 86, these ramps ending with an abrupt face 86b providing the desired notching effect. These axial immobilization notches 86 cooperate with a conjugated cut (aperture or indentation) 88 made in the PZT beam at the place where the notches will come in the definitive immobilization position.

In a comparable way, the radial immobilization notches 90 each comprise a ramp-shape inclined face 90a, directed in radial direction, in one direction for one for the notches 90 and in the opposite direction for the other notch 90, these ramps ending with an abrupt face 90b providing the notching effect with the PZT beam at the location of the conjugated cut 92 formed in the latter.

These notching geometries allow in particular the progressive positioning of the components (inertial mass 26 and PZT beam 22) at the time of assembly, with a two-dimensional axial and two-dimensional radial final blocking effect; the PZT beam 22, which is not compressed in the non-clamping enlarged portion 78, is free to move up to its final locking.

Figures 13, 14, 15:
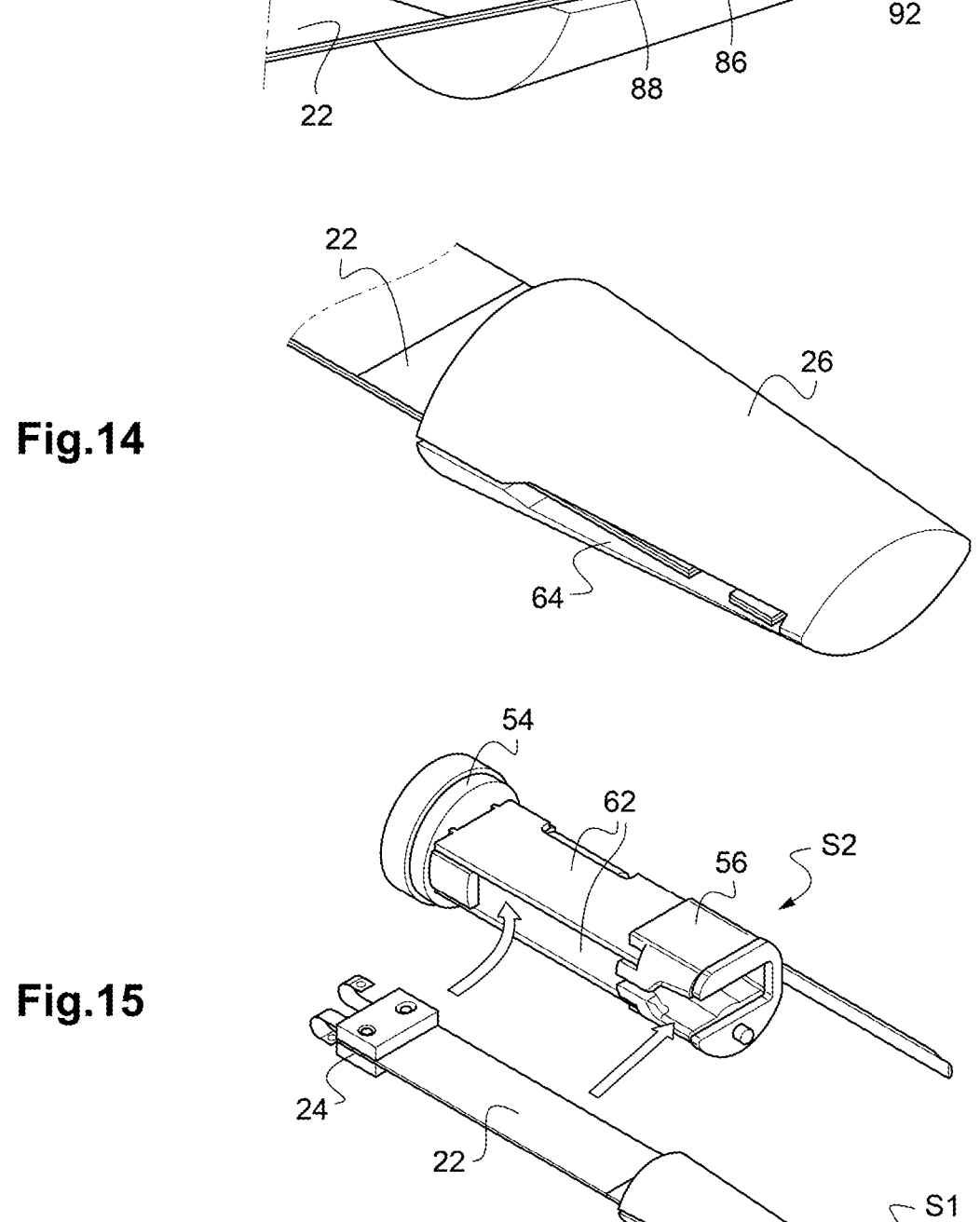
FIG. 13 is a perspective view, in partial cross-section, of the pendular unit of FIG. 10.
FIG. 14 is a perspective view showing the pendular unit of FIG. 10 in the final assembled form.
FIGS. 15 and 16 illustrate two steps of assembly of a leadless capsule with a PEH module comprising a pendular unit according to the invention.
Figure 16:
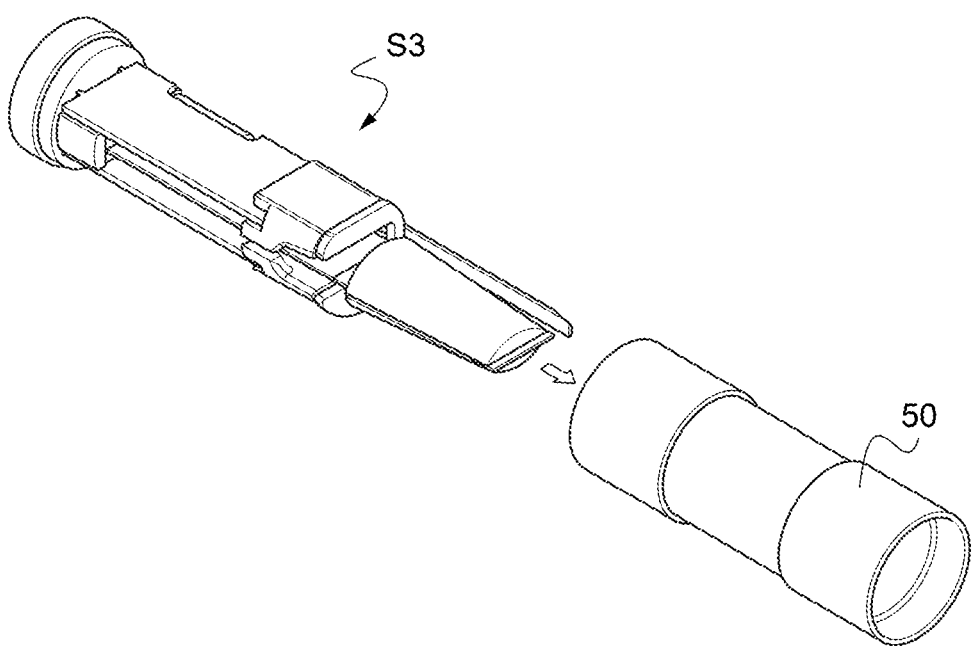
Figure 17:
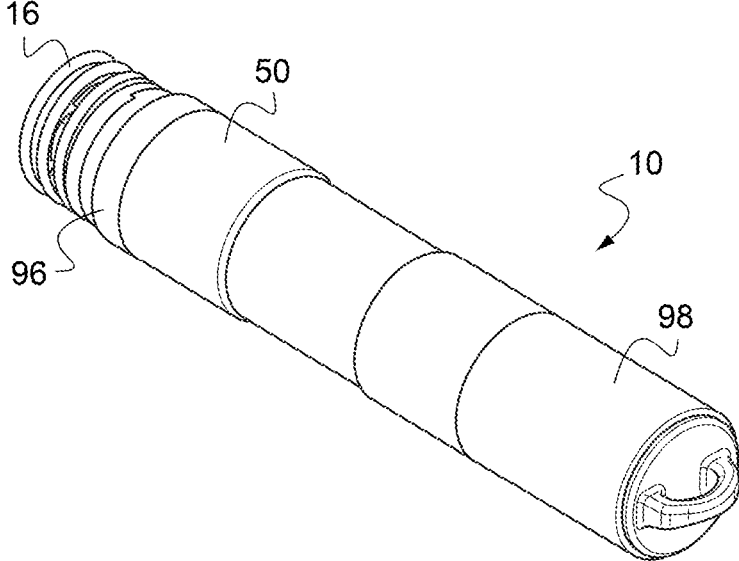
FIG. 17 illustrates the final implantable leadless capsule obtained at the end of the process.
Figure 18:
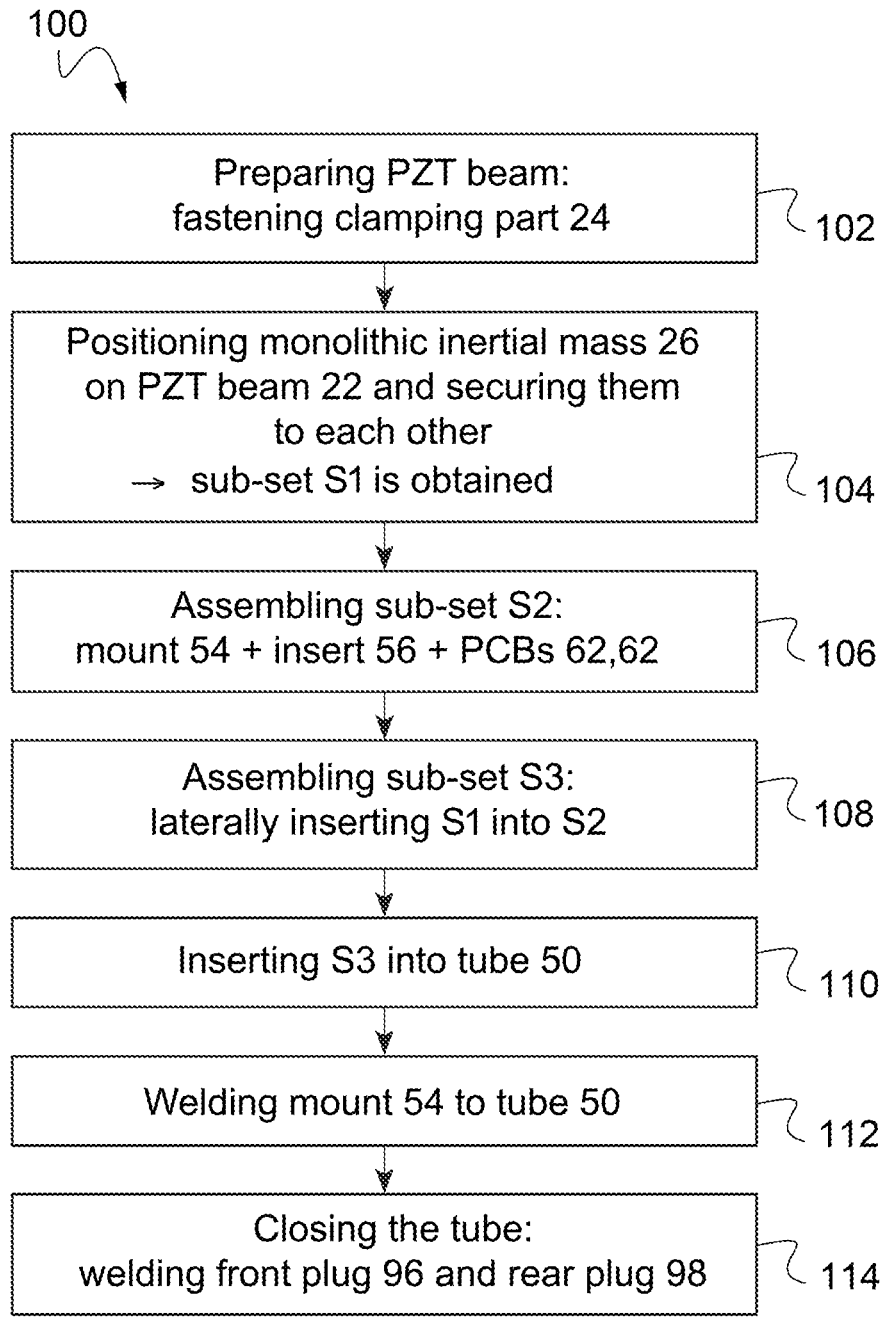
FIG. 18 is a flow diagram explaining the different steps of the process of assembling an implantable leadless capsule comprising a PEH module with a pendular unit according to the invention.

With reference to FIGS. 15 to 17 and to the flow diagram of FIG. 18 showing the different steps of the process, the way are manufactured and assembled the PEH module comprising the pendular unit provided with the just-described seismic mass, as well as the full leadless capsule integrating such a module.

The first step (block 102 in flow diagram 100 of FIG. 18) consists in preparing the PZT beam and in fastening clamping beam 24 at its proximal end.

The following step (block 104) consists in positioning on the PZT beam 22 the monolithic inertial mass 26 previously machined as described hereinabove, the PZT beam 22 being sandwiched within axial cavity 64, up to mutual securing of the inertial mass 26 and the PZT beam 22 according to the various techniques described hereinabove.

A first sub-set S1 is thus obtained (FIG. 15), which is made up of the PZT beam 22 with clamping part 24 at its proximal end and the inertial mass 26 at its distal end.

The following step (block 106) consists in assembling a sub-set S2 (FIG. 15) gathering mount 54 and insert 56, with the two PCBs 62 mounted between these two elements 54 and 56.

The following step (block 108) consists in gathering sub-sets S1 and S2 into one sub-set S3 (FIG. 16) by introducing sub-set S1 in the lateral space arranged between insert 56, mount 54 and the two PCBs 62 of sub-set S2.

The following step (block 110) consists in introducing this sub-set S3 into envelop tube 50 by axial translation (FIG. 16). Mount 54 is then welded to tube 50 (step 112), for example by means of peripheral laser shots.

The final step (block 114) consists in closing at its two ends the envelope tube 50 containing the pendular unit, by adding a front plug 96 carrying anchoring screw 16 of the leadless capsule and a rear plug 98. These plugs 96 and 98 are attached to tube 50 by peripheral laser weldings. The leadless capsule is then in its final assembled state, as illustrated in FIG. 17.

What is claimed is:

1. A pendular unit for a piezoelectric energy harvesting (PEH) module, the pendular unit comprising:
   a lead zirconate titanate (PZT) transducer beam that is elastically deformable in bending and that extends in an axial direction between a clamped proximal end and a free distal end; and
   an inertial mass mounted at the free distal end of the PZT transducer beam and mobile in a transverse direction, the pendular unit being adapted to convert a mechanical energy produced by oscillations of the pendular unit under an effect of external stresses undergone by the PEH module into an oscillating electrical signal collected by surface electrodes of the PZT transducer beam,
   wherein the inertial mass is a monolithic part including an axial slit forming a cavity, with two opposite longitudinal surfaces extending along a central axis of the inertial mass, the axial slit opening out on a proximal side of the inertial mass and receiving the free distal end of the PZT transducer beam,
   and wherein the axial slit forming said cavity comprises:
      on a proximal side, a clamping area in which the PZT transducer beam is secured between the two opposite longitudinal surfaces of the axial slit; and
      on a distal side, a non-clamping area.

2. The pendular unit of claim 1, wherein, over a length of the clamping area, the two opposite longitudinal surfaces comprise flat and parallel symmetrical surfaces separated by a constant radial spacing.

3. The pendular unit of claim 2, wherein the two opposite longitudinal surfaces comprise surfaces that widen along a length of the non-clamping area.

4. The pendular unit of claim 1, wherein the two opposite longitudinal surfaces are symmetrical surfaces radially separated by an increasing radial spacing in a direction proximal to distal along at least part of a length of the axial slit in a longitudinal direction, in such a way as to produce a progressive clamping of the PZT transducer beam, with a maximum clamping force in the clamping area and a zero clamping force in the non-clamping area.

5. The pendular unit of claim 1, wherein, in a radial direction, the axial slit also opens out in at least one of a side of the inertial mass.

6. The pendular unit of claim 1, wherein at least one of the two opposite longitudinal surfaces comprise at least one non-return notch provided with an axial and/or radial stop adapted to block the PZT transducer beam in a position in the axial slit.

7. The pendular unit of claim 6, wherein the PZT transducer beam comprises, in an area located between the two opposite longitudinal surfaces of the axial slit, at least one cut adapted to cooperate with an axial and/or radial stop for mating a non-return notch of the inertial mass.

8. The pendular unit of claim 1, wherein, in the clamping area, a minimum value of a radial spacing between the two opposite longitudinal surfaces is equal to a thickness of the PZT transducer beam, to within a negative clearance, in such a way as to exert on the PZT transducer beam a pinching force between the two opposite longitudinal surfaces.

9. The pendular unit of claim 8, wherein a pinching force of the PZT transducer beam exerted by the two opposite longitudinal surfaces is between 0.5 and 2 N/mm².

10. The pendular unit of claim 1, wherein the pendular unit is integrated to the PEH module, the PEH module comprising an elongated envelope tube containing the pendular unit.

11. The pendular unit of claim 10, wherein the PEH module is integrated to an autonomous device having a device body containing:

an electronic unit;

a power management circuit adapted to rectify and regulate the oscillating electric signal produced by the pendular unit of the PEH module to output a stabilized direct power voltage or current; and an energy storage component for powering the electronic unit, wherein said stabilized direct voltage or current provided by the power management circuit is used to power the electronic unit and/or to charge the energy storage component of the autonomous device.

12. The pendular unit of claim 11, wherein the autonomous device is an implantable autonomous capsule type active medical device comprising a capsule body with an element for its anchoring to a wall of a patient's organ, and wherein the external stresses to which is subjected the pendular unit of the PEH module are stresses applied to the capsule body under an effect of movements of said wall and/or flow rate variations of a flow in a surrounding environment.

13. A method for assembling a pendular unit for a piezoelectric energy harvesting (PEH) module, the pendular unit comprising a lead zirconate titanate (PZT) transducer beam that is elastically deformable in bending and an inertial mass mounted at a free distal end of the PZT transducer beam and mobile in a transverse direction, the method comprising the following steps:

a) obtaining an inertial mass by forming an axial slit in a mass of a monolithic part, the axial slit extending along a central axis of the inertial mass from a proximal end, thus forming two opposite longitudinal surfaces, the axial slit comprising successive cavities with different geometries, comprising: on a proximal side, a clamping area in which the PZT transducer beam is secured between the two opposite longitudinal surfaces of the axial slit; and on a distal side, a non-clamping area;

b) inserting into the axial slit the free distal end of the PZT transducer beam; and c) securing the free distal end of the PZT transducer beam to the monolithic part between the two opposite longitudinal surfaces of the axial slit in the non-clamping area.

14. The method of claim 13, wherein, at step a), forming the axial slit in the monolithic part is performed using a material removal technique selected among wire electro-erosion or disk machining; or using an additive material deposition technique selected among stereolithography (SLA), selective laser sintering (SLS), or fused deposition modeling (FDM).

15. The method of claim 13, wherein, at step c), securing the free distal end of the PZT transducer beam to the monolithic part is performed using a technique selected among: temperature deformation of the PZT transducer beam or of the monolithic part before insertion in step b) then return to room temperature after insertion in step b); elastic deformation of the monolithic part to enlarge the axial slit before insertion in step b) then release after the insertion in step b); bonding; crimping; and/or welding of an added link part.

\* \* \* \* \*